(12) United States Patent
Chopra et al.

(10) Patent No.: US 6,468,511 B1
(45) Date of Patent: Oct. 22, 2002

(54) EMULSIONS WITH NAPHTHALATE ESTERS

(75) Inventors: Suman Kumar Chopra, Dayton, NJ (US); Bhal Moghe, Whitehouse Station, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 09/575,484

(22) Filed: May 19, 2000

(51) Int. Cl.$^7$ .................................................. A61K 7/32
(52) U.S. Cl. ........................................ 424/65; 424/401
(58) Field of Search .................. 424/401, 65

(56) References Cited

U.S. PATENT DOCUMENTS

| | | | |
|---|---|---|---|
| 4,673,570 A | 6/1987 | Soldati | 424/66 |
| 4,822,602 A | 4/1989 | Sabatelli | 424/65 |
| 5,008,103 A | 4/1991 | Raleigh et al. | 424/66 |
| 5,216,033 A | 6/1993 | Pereira et al. | 514/844 |
| 5,292,503 A | 3/1994 | Raleigh et al. | 424/59 |
| 5,401,870 A | 3/1995 | Raleigh et al. | 556/445 |
| 5,599,533 A | 2/1997 | Stepniewski et al. | 424/78.02 |
| 5,919,437 A | 7/1999 | Lee et al. | 424/68 |
| 5,939,056 A | 8/1999 | Fletcher et al. | 424/65 |
| 5,989,531 A * | 11/1999 | Schamper et al. | 424/95 |
| 5,993,789 A | 11/1999 | Bonda et al. | 424/59 |
| 6,007,799 A | 12/1999 | Lee et al. | 424/65 |
| 6,033,651 A | 3/2000 | Dolak et al. | 424/65 |
| 6,060,546 A | 5/2000 | Powell et al. | 524/267 |
| 6,113,931 A * | 9/2000 | Bonda et al. | 424/401 |

FOREIGN PATENT DOCUMENTS

| | | |
|---|---|---|
| EP | 0291334 | 11/1988 |
| EP | 0512770 | 11/1992 |
| EP | WO 9219221 | 11/1992 |
| EP | WO 9858624 | 12/1998 |
| EP | 0940423 | 3/1999 |
| EP | WO 9951192 | 10/1999 |
| JP | 07076511 | 9/1993 |
| JP | 86772 | 3/2000 |
| WO | WO 0139732 | 6/2001 |

OTHER PUBLICATIONS

U.S. patent application Ser. No. 09/273,152, Potechin et al., filed Mar. 19, 1999.

* cited by examiner

*Primary Examiner*—Jose' G. Dees
*Assistant Examiner*—Konata M. George
(74) *Attorney, Agent, or Firm*—Rosemary M. Miano

(57) ABSTRACT

This invention relates to an anhydrous cosmetic composition comprising: (a) 15–33% of an external phase (also called the oil phase) which is made with at least one selected naphthalate organic ester; a volatile silicone based emulsifier; and a volatile silicone; and (b) 85–67% of an internal phase which is made with an active ingredient, such as an antiperspirant active, in a glycol solvent. For the external phase all or a major portion of what would have been a non-volatile silicone component has been replaced by the naphthalate ester. While a dimethicone copolyol is still included, the use of this particular naphthalate ester obviates the need for the use of any other non-ionic emulsifiers.

24 Claims, No Drawings and gel sticks), semi-solids (for example, gels and creams),

EMULSIONS WITH NAPHTHALATE ESTERS

FIELD OF THE INVENTION

This invention relates to cosmetic product, especially antiperspirant and/or deodorant products which contain an antiperspirant active ingredient and which provides better efficacy and stability without compromising aesthetics. The compositions are emulsions made with an external (or oil) phase and an internal phase which contains the active ingredient. These emulsions may be used to form gel, soft solid or roll-on products.

BACKGROUND OF THE INVENTION

A large variety of antiperspirant and/or deodorant formulations have been described in the patent literature and/or have been made commercially available. These products have included suspension as well as emulsions. Also various physical forms may be used such as solids (for example, wax and gel sticks), semi-solids (for example, gels and creams), liquids (for example, roll-on products) and sprays (both aerosol and non-aerosol).

In recent years a strong emphasis has been placed on improving both the performance of antiperspirant and/or deodorants, for example, the efficacy, aesthetics, and stability of these products. One of the particular problems is trying to obtain an emulsion product that has efficacy comparable to suspension products. A second problem is the stabilization of emulsion products to achieve a product that is shelf stable, but which releases an active ingredient in a timely manner. These problems have been caused, in part, by the use of non-volatile silicones used to match the refractive index of the two phases for clear systems or used for improving skin feel. The use of such non-volatile silicones (1) decreases the ability of the active ingredient to be released from the composition thereby decreasing efficacy, and (2) makes the emulsions so stable that the active is not released in a timely manner.

With regard to emulsions, U.S. Pat. No. 4,673,570 to Soldati describes uniform, clear gelled antiperspirant compositions, free of waxes wherein the emulsions comprise in combination a volatile silicone fluid, a silicone emulsifier (such as a mixture of cyclomethicone and dimethicone copolyol), a destabilizing auxiliary emulsifier, water, a non-volatile emollient (such as C10–C20 alkyl fatty esters and ethers), linear silicone fluids, a coupling agent (such as low molecular weight alcohols and glycols), an active antiperspirant component and other ancillary agents.

U.S. Pat. No. 5,008,103 to Raleigh et al describes water-in-oil antiperspirant emulsions having a discontinuous polar phase containing water and optionally containing an emulsifier with a hydrophilic-lipophilic balance (HLB value) greater than 8, and a volatile silicone continuous phase with a dimethicone copolyol emulsifier. The HLB parameter is a well known parameter the calculation of which is disclosed and explained in numerous references. For nonionic surfactants, data obtained by actual analysis is usually a more accurate measure of HLB values (rather than theoretical determinations). U.S. Pat. No. 5,401,870 to Raleigh et al and U.S. Pat. No. to 5,292,503 to Pereira et al describe similar subject matter.

U.S. Pat. No. 5,216,033 to Pereira et al describes a transparent water-in-oil emulsion containing a silicone phase with a dimethicone copolyol and an aqueous phase containing a refractive index "transparency structurant" to produce a refractive index matched clear emulsion. The transparency structurant is a C3–C8 polyhydric alcohol.

U.S. Pat. No. 5,599,533 to Stepniewski et al describes the use of silicone elastomer in an aqueous water-in-oil emulsion, but does not describe a clear emulsion.

U.S. Pat. No. 5,989,531 describes a liquid composition made with (a) an active phase comprising a selected glycol, a nonionic emulsifier having an HLB value greater than 8 and an antiperspirant and/or deodorant active; and (b) a silicone phase made with one or more of a dimethicone copolyols having an HLB less than 7 and nonionic emulsifiers having an HLB greater than 7, wherein the silicone phase has at least 10% silicone and the ratio of the silicone phase to he active phase is in the range of 1:1–1:4. Optional ingredients include the use of non-volatile silicones, volatile silicones and organic emollients.

U.S. Pat. No. 6,033,651 describes a single phase aqueous gel composition comprising 0.05–50% of a polysaccharide gellant, and 1–30% of an antiperspirant active ingredient solubilized in the aqueous single phase wherein the composition is formed with a water and an oil emulsion comprising a gelled aqueous phase comprising a polysaccharide gellant and an antiperspirant active ingredient solubilized in the aqueous single phase; and an oil phase.

Historically, suspension products such as sticks have exhibited better efficacy than emulsion products. Previous attempts have not successfully overcome the problems of improving efficacy and achieving satisfactory formation of emulsions. Thus, it is an object of this invention to provide improved anhydrous emulsions which exhibit improved efficacy which efficacy is comparable to that achieved in suspension products and, at the same time, have a stability profile that allows for satisfactory stability on the shelf. Another issue is the formation of emulsions which are stable on the shelf but which destabilize sufficiently after application to a skin surface so as to release an efficacious amount of an active ingredient. Thus, it is an object of the present invention to provide emulsions with those characteristics. It is also an object of this invention to provide gel or soft solid compositions which can, if desired, be formed into clear compositions. It is still another object of this invention to provide compositions that can, if desired, be formed into clear compositions without the use of microemulsions

SUMMARY OF THE INVENTION

This invention relates to an anhydrous cosmetic composition comprising:

(a) 15–33% of an external phase (also called the oil phase) which is made with at least one selected naphthalate organic ester; a volatile silicone based emulsifier; and a volatile silicone; and (b) 67–85% of an internal phase which is made with an active ingredient, such as an antiperspirant active, in a solvent (especially a glycol or polyglycol solvent) wherein the conductance of the composition is at least 250, particularly 300, more particularly 400 and especially 500 micro Siemens at a loading of at least 7% by weight level of antiperspirant active as measured by the test described below.

For the external phase all or a major portion of what would have been a non-volatile silicone component has been replaced by the naphthalate ester. While a dimethicone copolyol is still included, the use of this particular naphthalate ester obviates the need for the use of any other non-ionic emulsifiers. Also, while small amounts (for example, 0–5%) of a non-volatile silicone may be included, it is preferred that the compositions be made without the addition of non-volatile silicones.

DETAILED DESCRIPTION OF THE INVENTION

The emulsions of this invention comprise an external and an internal phase as described below:

External Phase comprising
(a) 0.1–25% (particularly 0.5–25% and more particularly 2.5–15%) of an organic naphthalate ester (especially 2,6-di-(ethylhexyl)naphthalate having a refractive index in the range of 1.43–1.60, which is not soluble in alcohol or glycols (except in minor amounts such as up to 1.0%)and which is capable of releasing an antiperspirant active to achieve a specified conductivity,
(b) a sufficient amount of a silicone copolyol to achieve a solids content of 0.25–10% (particularly 1.0–3.0%) wherein the silicone copolyol may be added with or without solvent;
(c) a sufficient amount of a volatile silicone (for example, a cyclomethicone such as a D5 cyclomethicone) to achieve a quantum sufficient ("q.s.") amount of the external phase as 15–33% (for example, wherein part of the volatile silicone may be added in a silicone copolyol which itself is obtained already mixed with a volatile silicone as a solvent, such as a 40–48% dimethicone copolyol in cyclomethicone);
(d) 0–5% of a silicone elastomer (on an actives basis); and
(e) 0–15%, particularly 0–10% and, more particularly, 0–5% of at least one emollient;

Internal Phase comprising
(a) 0.1–30% (particularly 0.1–25%, and more particularly 10–20%) of an antiperspirant active (on an anhydrous basis); and
(b) a sufficient amount of a solvent component to dissolve the cosmetically active ingredient and to complete the internal phase (for example, a glycol component to dissolve an antiperspirant active), with a maximum amount being about 70% of solvent for a deodorant product and abut 80% for an antiperspirant product;

wherein the ratio of the external phase to the internal phase is in the range of 1:1–1:4 and all amounts are in percent by weight based on the total weight of the composition.

Additionally, other optional ingredients can be added to the internal phase such as 0–10% of an alcohol such as ethanol, 0–5% fragrance, and 0–5% of a non-ionic emulsifier.

Particular compositions include (a) a composition wherein the internal phase comprises up to 7% antiperspirant active and 50–80% glycol component; and (b) a composition wherein the internal phase comprises 7–25% of an antiperspirant active and 35–55% of a glycol component.

Optionally, one or more of each of fragrance, color, preservative can be added to the appropriate phase as is known to those skilled in the art.

In general the organic naphthalate esters can be described as a monoester, diester and/or polyester of a naphthalene dicarboxylic acid and which are reaction products of
(i) a naphthalene dicarboxylic acid having the structure: $HO_2C$—Q—$CO_2H$ where Q is a naphthalene; and
(ii) an alcohol having the structure $R^1$—OH, or a diol having the structure HO—$R^2$—OH, or a polyglycol having the structure HO—$R^3$—(—O—$R^2$—)$_m$—OH, wherein $R^1$ is an alkyl group, straight chain or branched, having 1 to 22 carbon atoms, $R^2$ and $R^3$, may be the same or different, and are each an alkylene group, having 1 to 6 carbon atoms, and wherein m and n are each 1 to about 100, preferably 1 to about 10, more preferably 2 to about 7, or a mixture thereof.

A diester of the present invention has the structure: $R^1O_2C$—Q—$CO_2R^1$ wherein $R^1$ and Q have the same meanings as defined above.

The diesters and polyesters of naphthalene dicarboxylic acids that are of interest include those of the following Formula I:

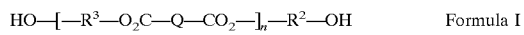

HO—[—$R^3$—$O_2C$—Q—$CO_2$—]$_n$—$R^2$—OH    Formula I wherein $R^2$ and $R^3$, may be the same or different, are each an alkylene group having 1 to 6 carbon atoms, and n=1 to about 100, preferably 1 to about 10, more preferably 2 to about 7.

Alternatively, the diesters and polyesters used in the present invention can be end-capped with an alcohol or an acid. The end-capped polyesters have a Formula II:

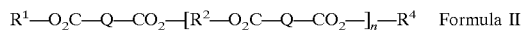

$R^1$—$O_2C$—Q—$CO_2$—[$R^2$—$O_2C$—Q—$CO_2$—]$_n$—$R^4$    Formula II wherein $R^1$ and $R^2$ and n are as defined above, with reference to Formula (I) and $R^4$ is independently selected from the same group as defined for $R^1$ in Formula I.

The preferred diesters and polyesters of the present invention have a weight average molecular weight of about 244 to about 4000, and more preferably about 450 to about 1500. To achieve the full advantage of the present invention, the diester or polyester has a weight average molecular weight of about 500 to about 1000.

The naphthalene dicarboxylic acid is selected from the group consisting of 1,2-naphthalene dicarboxylic acid; 1,3-naphthalene dicarboxylic acid; 1,4-naphthalene dicarboxylic acid; 1,5-naphthalene dicarboxylic acid; 1,6-naphthalene dicarboxylic acid; 1,7-naphthalene dicarboxylic acid; 1,8-naphthalene dicarboxylic acid; 2,3-naphthalene dicarboxylic acid; 2,6-naphthalene dicarboxylic acid; 2,7-naphthalene dicarboxylic acid, and mixtures thereof. Preferred dicarboxylic acids are the 2,6-, 1,5- and 1,8-naphthalene dicarboxylic acids.

The alcohol $R^1$—OH can be, for example, methanol, ethanol, propanol, isopropyl alcohol, n-butanol, sec-butanol, isobutyl alcohol, tert-butyl alcohol, amyl alcohol, 1-hexanol, 1-octanol, 1-decanol, isodecyl alcohol, 1-undecanol, 1-dodecanol, 1-tridecyl alcohol, 1-tetradecanol, 1-hexadecanol, 1-octadecanol, 1-eicosonol, 1-decosonol, 2-ethylhexyl alcohol, 2-butyloctanol, 2-butyldecanol, 2-hexyldecanol, 2-octyldecanol, 2-hexyldodecanol, 2-octyldodecanol, 2-decyltetradecanol, and mixtures thereof.

The glycol component is at least one member selected from the group consisting of glycols and polyglycol such as, for example, ethylene glycol, propylene glycol, 1,2-propanediol, diethylene glycol, triethylene glycol, tetraethylene glycol, dipropylene glycol, tripropylene glycol, methyl propanediol, 1,6-hexanediol, 1,3-butanediol, 1,4-butanediol, PEG-4 through PEG-100, PPG-9 through PPG-34, pentylene glycol, neopentyl glycol, trimethylpropanediol, 1,4-cyclohexanedimethanol, 2,2-dimethyl-1,3-propanediol, 2,2,4,4-tetramethyl-1,3-cyclobutanediol, and mixtures thereof.

Optionally up to 75% of the naphthalate portion of the composition can be substituted by an emollient selected from the group consisting of:
(a) fats and oils which are the glyceryl esters of fatty acids, or triglycerides, normally found in animal and plant tissues, including those which have been hydrogenated to reduce or eliminate unsaturation. Also included are synthetically prepared esters of glycerin and fatty acids. Isolated and purified fatty acids can be esterified with glycerin to yield mono-, di-, and triglycerides. These are relatively pure fats which differ only slightly from the fats and oils found in nature. The general structure may be represented by Formula VI:

Formula VI

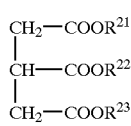

wherein each of $R^{21}$, $R^{22}$, and $R^{23}$ may be the same or different and have a carbon chain length (saturated or unsaturated) of 7 to 30. Specific examples include peanut oil, sesame oil, avocado oil, coconut, cocoa butter, almond oil, safflower oil, corn oil, cotton seed oil, castor oil, hydrogenated castor oil, olive oil, jojoba oil, cod liver oil, palm oil, soybean oil, wheat germ oil, linseed oil, and sunflower seed oil.

(b) hydrocarbons which are a group of compounds containing only carbon and hydrogen. These are derived from petrochemicals. Their structures can vary widely and include aliphatic, alicyclic and aromatic compounds. Specific examples include paraffin, petrolatum, hydrogenated polyisobutene, and mineral oil.

(c) esters which chemically, are the covalent compounds formed between acids and alcohols. Esters can be formed from almost all acids (carboxylic and inorganic) and any alcohol. Esters here include those derived from carboxylic acids and an alcohol. The general structure would be $R^{40}CO$—$OR^{50}$. The total number of carbons for $R^{40}$ and $R^{50}$ together can vary from 7 to 50 (particularly 14–30) and can be saturated or unsaturated, straight chained or branched. Other esters of interest include certain benzoates, fumarates, and esters with glycol portions or alkoxylated portions. Specific examples include isopropyl myristate, isopropyl palmitate, isopropyl stearate, isopropyl isostearate, butyl stearate, octyl stearate, hexyl laurate, cetyl stearate, diisopropyl adipate, isodecyl oleate, diisopropyl sebacate, isostearyl lactate, $C_{12-15}$ alkyl benzoates, myreth-3 myristate, dioctyl malate, neopentyl glycol diheptanoate, dipropylene glycol dibenzoate, $C_{12-15}$ alcohols lactate, isohexyl decanoate, isohexyl caprate, diethylene glycol dioctanoate, octyl isononanoate, isodecyl octanoate, diethylene glycol diisononanoate, isononyl isononanoate, isostearyl isostearate, behenyl behenate, $C_{12-15}$ alkyl fumarate, laureth-2 benzoate, octyldodecyl myristate, cetyl ricinoleate, myristyl myristate;

(d) adipic acid blends selected from the group consisting of trimethyl pentanediol/adipic acid copolymer (LEXOREZ TL8 from Inolex, Philadelphia, Pa.); trimethyl pentanediol/adipic acid/isononanoic acid copolymer (LEXOREZ TC8); and adipic acid/diethylene glycol/glycerin crosspolymer (LEXOREZ 100).

(e) lanolin and its derivatives which are a complex esterified mixture of high molecular weight esters of (hydroxylated) fatty acids with aliphatic and alicyclic alcohols and sterols as well as propoxylated and/or butoxylated species. Specific examples include lanolin, lanolin oil, lanolin wax, lanolin alcohols, lanolin fatty acids, isopropyl lanolate, propoxylated lanolin, butoxylated lanolin, and acetylated lanolin alcohols.

(f) mixtures and blends of two or more of the foregoing.

Particular examples of emollients for the silicone phase include organic emollients selected from: (1) propoxylated alcohols such as PPG-3 myristyl ether and PPG-14 butyl ether; (2) fats and oils such as avocado oil and mink oil; (3) hydrocarbons such as mineral oil, isoparaffins, hydrogenated polyisobutene, and squalane, particularly straight or branched chain hydrocarbons having 10–35 carbons; (4) lanolin and lanolin derivatives such as lanolin, lanolin oil; and (5) fatty esters such as isopropyl myristate, C12–15 alkyl benzoate, dioctyl adipate, and octylmethoxycinnamate.

The emollient or emollient mixture or blend thereof incorporated in compositions according to the present invention can, illustratively, be included in amounts of 0–15%, particularly 1–10%, more particularly 1–5% and, even more particularly, 2–3% by weight, based on the total weight of the composition.

For the silicone copolyols, dimethicone copolyols are of special interest. The dimethicone copolyols are of various types. These include copolyols of the following Formulae IA and IIA. Formula I materials may be represented by:

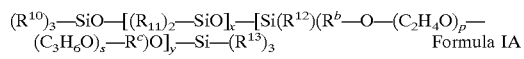

Formula IA wherein each of $R^{10}$, $R^{11}$, $R^{12}$ and $R^{13}$ may be the same or different and each is selected from the group consisting of C1–C6 alkyl; $R^b$ is the radical —$C_mH_{2m}$—; $R^c$ is a terminating radical which can be hydrogen, an alkyl group of one to six carbon atoms, an ester group such as acyl, or an aryl group such as phenyl; m has a value of two to eight; p and s have values such that the oxyalkylene segment —$(C_2H_4O)_p$—$(C_3H_6O)_s$— has a molecular weight in the range of 200 to 5,000; the segment preferably having fifty to one hundred mole percent of oxyethylene units —$(C_2H_4O)_p$— and one to fifty mole percent of oxypropylene units —$(C_3H_6O)_s$—; x has a value of 8 to 400; and y has a value of 2 to 40. Preferably each of $R^{10}$, $R^{11}$, $R^{12}$ and $R^{13}$ is a methyl group; $R^c$ is H; m is preferably three or four whereby the group $R^b$ is most preferably the radical —$(CH_2)_3$—; and the values of p and s are such as to provide a molecular weight of the oxyalkylene segment —$(C_2H_4O)_p$—$(C_3H_6O)_s$— of between about 1,000 to 3,000. Most preferably p and s should each have a value of about 18 to 28.

A second siloxane polyether (copolyol) has the Formula IIA:

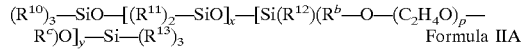

Formula IIA wherein p has a value of 6 to 16; x has a value of 6 to 100; and y has a value of 1 to 20 and the other moieties have the same definition as defined in Formula I.

It should be understood that in both Formulas I and II shown above, that the siloxane-oxyalkylene copolymers of the present invention may, in alternate embodiments, take the form of endblocked polyethers in which the linking group $R^b$, the oxyalkylene segments, and the terminating radical $R^c$ occupy positions bonded to the ends of the siloxane chain, rather than being bonded to a silicon atom in the siloxane chain. Thus, one or more of the $R^{10}$, $R^{11}$, $R^{12}$ and $R^{13}$ substituents which are attached to the two terminal silicon atoms at the end of the siloxane chain can be substituted with the segment —$R^b$—O—$(C_2H_4O)_p$—$(C_3H_6O)_s$—$R^c$ or with the segment —$R^b$—O—$(C_2H_4O)_p$—$R^c$. In some instances, it may be desirable to provide the segment —$R^b$—O—$(C_2H_4O)_p$—$(C_3H_6O)_s$—$R^c$ or the segment —$R^b$—O—$(C_2H_4O)_p$—$R^c$ at locations which are in the siloxane chain as well as at locations at one or both of the siloxane chain ends.

Particular examples of suitable dimethicone copolyols are available either commercially or experimentally from a variety of suppliers including Dow Corning Corporation, Midland, Mich.; General Electric Company, Waterford, N.Y.; Witco Corp., Greenwich, Conn.; and Goldschmidt Chemical Corporation, Hopewell, Va. Examples of specific products include DOW CORNING® 5225C from Dow Corning which is a 10% dimethicone copolyol in cyclomethicone; DOW CORNING® 2-5185C which is a 45–49% dimethicone copolyol in cyclomethicone; SILWET L-7622 from Witco; ABIL EM97 from Goldschmidt which is a 85% dimethicone copolyol in D5 cyclomethicone; and various dimethicone copolyols available either commercially or in the literature.

It should also be noted that various concentrations of the dimethicone copolyols in cyclomethicone can be used. While a concentration of 10% in cyclomethicone is frequently seen commercially, other concentrations can be made by stripping off the cyclomethicone or adding additional cyclomethicone. The higher concentration materials such as DOW CORNING® 2-5185 material is of particular interest.

By volatile silicone material is meant a material that has a measurable vapor pressure at ambient temperature. For the volatile silicone portion, examples of volatile silicones (particularly silicones with a boiling point of 250 degrees C. or less at atmospheric pressure) include cyclomethicone (especially cyclopentasiloxane, also called "D5"), "hexamethyldisiloxane", and low viscosity dimethicone (for example, Dow Corning® 200 fluid having a viscosity of 1–200 centistokes). Such volatile silicones include conventional cyclic and linear volatile silicones Illustratively, and not by way of limitation, the volatile silicones are one or more members selected from the group consisting of cyclic polydimethylsiloxanes such as those represented by Formula III:

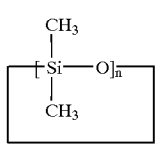

Formula III where n is an integer with a value of 3–7, particularly 5–6. For example, DC-245 fluid (or the DC-345 version) from Dow Corning Corporation (Midland, Mich.) is a type of cyclomethicone which can be used. These include a tetramer (or octylmethylcyclotetrasiloxane) and a pentamer (or decamethylcyclopentasiloxane). The volatile linear silicones can also be included in this group of volatile silicones and are one or more members selected from the group consisting of linear polydimethylsiloxanes such as those represented by Formula IV:

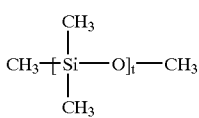

Formula IV and t is selected to obtain a viscosity of 1–200 centistokes.

It is also possible to include a silicone elastomer in the external phase. Suitable elastomers include those described in copending PCT case WO 99/51192, incorporated by reference herein. Particular examples of suitable elastomers are SFE 167, a cetearyl dimethicone/vinyl dimethicone crosspolymer from GE Silicones (Waterford, N.Y.); SFE168, a cyclomethicone (and) dimethicone/vinyl dimethicone crosspolymer from GE Silicones; vinyl dimethicone crosspolymers such as those available from Shin Etsu Silicones of America (Akron, Ohio) under trade names KSG-15 (cyclomethicone (and) dimethicone/vinyl dimethicone crosspolymer), KSG-16 (dimethicone (and) dimethicone/ vinyl dimethicone crosspolymer), KSG-17 (cyclomethicone (and) dimethicone/vinyl dimethicone crosspolymer), KSG-18 (phenyl trimethicone (and) dimethicone/phenyl vinyl dimethicone crosspolymer); and KSG-20 (dimethicone copolyol crosspolymer; dimethicone/vinyl dimethicone crosspolymer from Dow Coming Corporation (Midland, Mich.) under trade name Dow Coming 9506 Cosmetic Powder; and a mixture of cyclomethicone and stearyl-vinyl/ hydromethylsiloxane copolymer available from Grant Industries, Inc. (Elmwood Park, N.J.) under the trade name Gransil SR-CYC.

For the antiperspirant active used in the active phase various antiperspirant active materials that can be utilized according to the present invention provided that they are soluble at a suitable concentration in the active phase. These include conventional aluminum and aluminum/zirconium salts, as well as aluminum/zirconium salts complexed with a neutral amino acid such as glycine, as known in the art. See each of European Patent Application Number. 512,770 A1 and PCT case WO 92/19221, the contents of each of which are incorporated herein by reference in their entirety, for disclosure of antiperspirant active materials. The antiperspirant active materials disclosed therein, including the acidic antiperspirant materials, can be incorporated in the compositions of the present invention if they are soluble in the active phase. Suitable materials include (but are not limited to) aluminum chlorides (various types including, for example, anhydrous form, hydrated form, etc.), zirconyl hydroxychlorides, zirconyl oxychlorides, basic aluminum chlorides, basic aluminum chlorides combined with zirconyl oxychlorides and hydroxychlorides, and organic complexes of each of basic aluminum chlorides with or without zirconyl oxychlorides and hydroxychlorides and mixtures of any of the foregoing. These include, by way of example (and not of a limiting nature), aluminum chlorohydrate, aluminum chloride, aluminum sesquichlorohydrate, aluminum chlorohydrol-propylene glycol complex, zirconyl hydroxychloride, aluminum-zirconium glycine complex (for example, aluminum zirconium trichlorohydrex gly, aluminum zirconium pentachlorohydrex gly, aluminum zirconium tetrachlorohydrex gly and aluminum zirconium octochlorohydrex gly), aluminum dichlorohydrate, aluminum chlorohydrex PG, aluminum chlorohydrex PEG, aluminum dichlorohydrex PG, aluminum dichlorohydrex PEG, aluminum zirconium trichlorohydrex gly propylene glycol complex, aluminum zirconium trichlorohydrex gly dipropylene glycol complex, aluminum zirconium tetrachlorohydrex gly propylene glycol complex, aluminum zirconium tetrachlorohydrex gly dipropylene glycol complex, and mixtures of any of the foregoing. The aluminum-containing materials can be commonly referred to as antiperspirant active aluminum salts. Generally, the foregoing metal antiperspirant active materials are antiperspirant active metal salts. In the embodiments which are antiperspirant compositions according to the present invention, such compositions need not include aluminum-containing metal salts, and can include other antiperspirant active materials, including other antiperspirant active metal salts. Generally, Category I active antiperspirant ingredients listed in the Food and Drug Administration's Monograph on antiperspirant drugs for over-the-counter human use can be used. In addition, any new drug, not listed in the Monograph, such as tin or titanium salts used alone or in combination with aluminum compounds (for example, aluminum-stannous chlorohydrates), aluminum nitratohydrate and its combination with zirconyl hydroxychlorides and nitrates, can be incorporated as an antiperspirant active ingredient in antiperspirant compositions according to the present invention. Preferred antiperspirant actives that can be incorporated in the compositions of the present invention include the enhanced efficacy aluminum salts and the enhanced efficacy aluminum/zirconium salt-glycine materials, having enhanced efficacy due to improved molecular distribution, known in the art and discussed, for example, in PCT No.

WO92/19221, the contents of which are incorporated by reference in their entirety herein.

Antiperspirant actives can be incorporated into compositions according to the present invention in amounts in the range of 0.1–30% (on an anhydrous solids basis), particularly 0.1–25%, preferably 5–25%, wherein the amounts are percent by weight based on the total weight of the composition. The amount used will depend on the formulation of the composition. For example, at amounts in the lower end of the broader range (for example, 0.1–5%), the antiperspirant active material will not substantially reduce the flow of perspiration, but will reduce malodor, for example, by acting as a deodorant material. Compositions made with amounts of active in the higher end of the range (for example, 9–25%) will be considered antiperspirants.

One type of active is selected from the group consisting of Westchlor A2Z4105 from Westwood Chemicals (Middletown, N.Y.) wherein the active material is a 28–35% concentration of active in propylene glycol in a 30:70 phase ratio. This active material may be used in amounts as high as 20–24% in the final cosmetic composition. In these formulations with a higher active level, the organic phase can be maintained at a higher level of up to 45%.

Deodorant active materials can be selected from several types of materials:
(a) lesser amounts of antiperspirant actives, such as in the range of 0.1–5.0 percent by weight based on the total weight of the composition;
(b) fragrances, such as in the range of 0.5–3.0 percent by weight based on the total weight of the composition;
(c) effective amounts of antimicrobial agents, for example, 0.05–5.0 percent (particularly 0.1–1% and, more particularly, 0.25–1.0%) by weight based on the total weight of the composition; examples include bacteriostatic quaternary ammonium compounds (such as cetyl trimethyl-ammonium bromide, and cetyl pyridinium chloride), 2,4,4'-trichloro-2'-hydroxydiphenylether (Triclosan), N-(4-chlorophenyl)-N'-(3,4-dichlorophenyl)urea (Triclocarban), silver halides, octoxyglycerin (SENSIVA™SC 50) and various zinc salts (for example, zinc ricinoleate). Triclosan or Triclocarban can, illustratively, be included in an amount of from 0.05% to about 0.5% by weight, of the total weight of the composition.

The glycol or polyglycol is selected from the group consisting of ethylene glycol, propylene glycol, 1,2-propanediol, diethylene glycol, triethylene glycol, tetraethylene glycol, dipropylene glycol, tripropylene glycol, methyl propanediol, 1,6-hexanediol, 1,3-butanediol, 1,4-butanediol, PEG-4 through PEG-100, PPG-9 through PPG-34, pentylene glycol, neopentyl glycol, trimethylpropanediol, 1,4-cyclohexanedimethanol, 2,2-dimethyl-1,3-propanediol, 2,2,4,4-tetramethyl-1,3-cyclobutanediol, and mixtures thereof. More particular examples of the glycol component include one or more members of the group consisting of propylene glycol, dipropylene glycol, tripropylene glycol, 2-methyl-1,3-propanediol, methyl propylene glycol, low molecular weight (less than 600) polyethylene glycol, low molecular weight (less than 600) polypropylene glycols, and mixtures of any of the foregoing. Propylene glycol is of particular interest because the antiperspirant active is more soluble in this type of glycol. Tripropylene glycol has lower irritancy, but the antiperspirant active is not as soluble in this glycol. Mixtures of glycols may be used to balance these desirable properties.

The compositions of the present invention can include other optional ingredients to improve the aesthetics and/or performance of the cosmetic compositions of the invention. These include colorants, fillers, fragrances, emollients, masking agents, etc. Such one or more other optional ingredients can be added to the internal or external phases or both in appropriate amounts. For example, fragrances will frequently be partitioned to both the external and internal phases regardless of when or to what phase (or final product) the fragrance is added.

While the mechanism of why this invention provides improved efficacy is not completely understood, it is believed that the invention solves two problems. The first problem is the barrier problem which is caused, in significant part, by the presence of a non-volatile silicone component. The second problem is the stability of the emulsion which, if too stable, results in failure of the antiperspirant to be released and a reduction in efficacy. This invention overcomes both of these problems with (a) the significant reduction or, preferably, total elimination of the non-volatile silicone component that is frequently used in antiperspirant and/or deodorant products and (b) the creation of emulsion that exhibit satisfactory stability on the shelf and yet break down when applied to the skin to release the antiperspirant active allow for improved performance. As an additional benefit, the formulations of this invention may be made as clear products without the use of microemulsions.

The release of antiperspirant actives into the sweat is a significant event in the development of an antiperspirant effect. The magnitude of the antiperspirant effect is related to the concentration of the antiperspirant salt in the sweat, and therefore measuring the concentration of antiperspirant salt can provide an estimate of antiperspirant efficacy. A variety of methods can be used to evaluate antiperspirant salt concentration, ranging from atomic absorption, ICP, and HPLC to solution conductance of aqueous films. The later method is especially well suited for measuring the release of small amounts of antiperspirant salts. The methods outlined below use solution conductance to estimate antiperspirant salt release upon short exposures to deionized water.

As noted above, the conductance of the compositions of the invention is defined with reference to a value of at least 250 micro Siemens/cm/ml when the composition is loaded with at least 7% of an antiperspirant active (such as the antiperspirant actives listed above) and when the conductance is measured by a fixed geometry test. For purposes of clarification is should be explained that there are a variety of tests and test conditions that can be used to evaluate:
(1) "Conductance" is defined as an absolute measure of current flow through a solution with the dimensions of micro Siemens/cm, which value is independent of probe geometry. This value is divided by the volume (in ml) of applied water to give the conductance number with the units of micro Siemens/cm/ml. This test is deemed a more reproducible measurement since it references a set of fixed dimensions and units.

(2) Alternatively, "conductivity" as a measure of current flow through a solution without reference to probe geometry, and which is measured in micro Siemens. This test is convenient for quick screening of solutions.

Standard Test for Thin Film Conductivity

One test for conductivity is called herein the "standard" test. A non-conducting plastic block (for example, made from PLEXIGLASS® material) to form an oral shaped well 12.2 cm×2.5 cm with a depth of 100 microns. This depth corresponds to the mean thickness of an antiperspirant product applied to the underarm of a human person during real use conditions (approximately 50 to 100 microns). An aliquot of test sample is placed in the well of the block sufficient to fill the well to the brim. Excess sample is scraped off by running a flat edged instrument over the surface of the block. The sample block, with the product film, is then either (a) equilibrated at room temperature for two hours or (b) placed in a synthetic underarm to simulate in vivo conditions. If method (b) is used, the air temperature inside the synthetic underarm is maintained at 33 to 35° C. and a relative humidity of 85 to 95%, and the sample blocks are placed on a temperature controlled surface maintained at body temperature (37° C.). These conditions closely approximate the temperature gradients normally found in the underarm. Samples are equilibrated in either the (a) or (b) environments for two hours prior to measurement of antiperspirant salt release by solution conductivity. After two hours the sample blocks are removed from the controlled environment and placed on a stage for conductivity measurement. An aliquot of 250 microliters of water with a resistance of at least 17 mega Ohms is placed on the surface of the sample film, and the conductance of the water is measured as a function of time with a Skicon 200 Skin surface Hygrometer (I.B.S. Co., Ltd., Shizuoka-ken, 430, Japan) using an Elsnau (MT-8C Probe) electrode (Todd Maibach & Associates, San Francisco, Calif.). The electrode is positioned so that it touches the bottom of the test sample in the well. Conductivity is measured in micro Siemens at 3.5 MHz. Data is collected at 0.1 sec intervals for approximately 100 sec. Solution conductivity after 10 seconds of exposure to the water is used to compare the release of active salt for different formulations This method is believed to be particularly useful for evaluating the release of antiperspirant salts in the absence of other salts. The standard method is useful as a quick screening tool for active salt release studies. A solution conductivity of approximately 400 or greater micro Siemens at 10 sec after application of the water droplet to the surface of the test sample, can be considered evidence of significant release of the antiperspirant active salt from the film surface and correlates with improved antiperspirant efficacy.

Fixed Geometry Test for Thin Film Conductance

One of the limitations of the Standard Test is that the area of the water droplet is not controlled and, therefore, the apparent conductance (which is measured as conductivity because the water volume is not controlled) is dependent on droplet spreading. This will lead to an underestimate of the actual solution conductance (and therefore antiperspirant salt release), of water drops which spread significantly. In order to measure the absolute concentration of the antiperspirant salts the spreading of the water drop must be stopped. This can be accomplished by placing a well of know dimensions on the surface of the product film to establish an area of constant size that is exposed to the water droplet. A more predictable test is needed, such as the Fixed Geometry Test.

The Fixed Geometry Test uses the same basic technique as the Standard Test in terms of preparation of the test well, addition of the test sample and equilibration of the sample to a selected temperature. Instead of allowing the water to flow freely on the surface of the test film, however, a second structure of non-conducing plastic predrilled with holes of a fixed diameter is clamped over the well block. The second structure with holes is also made of a non-conducting material (such as PLEXIGLAS material), is open on both ends and has an internal diameter of 1.905 cm. The bottom of each predrilled hole is fitted with a small O-ring to prevent leakage of the water. A 400 microliter aliquot of water (rather than the 250 microliter aliquot used in the Standard Test) with a resistance of 17 mega Ohms is then placed in the hole to cover the test sample. This will normally result in a liquid height for water of about 1.4 mm. The Elsnau probe is positioned through the drilled hole so that the bottom of the probe rests on the bottom of the well at a right angle. Because of the fixed shape, data can be obtained as conductance in micro Siemens/cm/ml using the method described for calculation.

As will be appreciated by those skilled in the art, a variety of other shapes, sizes and orientations of electrodes can be used. In another variation on the Fixed Geometry Test, thin gold wires (99% purity, set of 2, each about 1 mm in diameter) can be constructed to be in parallel with the surface of the water (and covered by the water) and conductance can be measured.

The electrode used in both types of tests must be calibrated so that a conductivity in micro Siemens can be obtained. Such calibration with a salt solutions in water of known conductance is known to those skilled in the art.

While different readings can be obtained depending on the thickness of the films, the test used, etc. it is important to establish a standard test for purposes of defining conductivity according to this invention. The Fixed Geometry Test is set as the defining test because it is believed to be more reproducible. Thus a minimum conductance value of 250 micro Siemens/cm/ml is the lower limit. Interestingly, minimum values for the Standard Test seemed to run about 400 micro Siemens due to the way the test was conducted. For the data described here, samples should be placed in a chamber at the humidity and elevated temperature conditions described above for about 2 hours. Samples not subjected to elevated temperatures should give higher values.

An average efficacy gel having a water contest of greater than 35%(such as Gillette's Right Guard Antiperspirant Gel) was compared with an improved gel made according to Example 3, below. The average efficacy gel has a standard conductivity of 295±35 micro Siemens at 10 seconds and a fixed geometry conductivity of 121±47 micro Siemens/cm/ml at 10 seconds. The improved formulation made according to this invention had a standard conductivity of 1884±225 micro Siemens at 10 seconds and a fixed geometry conductance of 1213±43 micro Siemens/cm/ml at 10 seconds. The improved formulation was ranked as above average in efficacy in a clinical test whereas the average gel was ranked as average in efficacy in a clinical test.

While it is not known precisely how the compositions of this invention work, it has been observed that they have a combination of two important properties. These compositions exhibit superior stability on the shelf and yet degrade on contact with the skin to release the active ingredient with a higher level of efficacy than is usually achieved. The deodorant and/or antiperspirant compositions disclosed in this invention form metastable emulsions when deposited on the skin. The decomposition of these emulsions upon application can be assessed by the thin film conductance method described herein. In another test the superiority of this invention is evaluated by applying test on skin, waiting 30 minutes and examining the product film under the microscope. Comparison to another formulations containing an antiperspirant active of low efficacy shows that the emulsions of effective formulations break up on the skin while the emulsions of the low efficacy samples remain intact.

Particular formulations of interest include:

Formulation A

External Phase comprising
- (a) 3.0–15% of 2,6-di-(ethylhexyl)naphthalate;
- (b) 1.5–3.0% of a 48% dimethicone copolyol in cyclomethicone or 0.1–7% (particularly 2–5%) of a 40% dimethicone copolyol in cyclomethicone);
- (c) 4.0–16% of a volatile silicone (for example, a cyclomethicone such as a D5 cyclomethicone); and
- (d) 0–1% of a silicone elastomer.

Internal Phase comprising
- (a) 9.0–20% of an antiperspirant active (on an anhydrous basis); and
- (b) a sufficient amount (35–55%) of a glycol component to dissolve the antiperspirant active and complete the internal phase;

wherein the ratio of the external phase to the internal phase is in the range of 1:1–1:4.

Formulation B

External Phase comprising
- (a) 10–15% of 2,6-di-(ethylhexyl)naphthalate;
- (b) 2–3% of a 40% dimethicone copolyol in cyclomethicone; and
- (c) 8–10% of a volatile silicone (for example, a cyclomethicone such as a D5 cyclomethicone).

Internal Phase comprising
- (a) 12–15% of an antiperspirant active (on an anhydrous basis); and
- (b) a sufficient amount (30–39%) of a glycol component to dissolve the antiperspirant active and complete the internal phase;

wherein the ratio of the external phase to the internal phase is in the range of 1:1–1:4.

Formulation C

External Phase comprising
- (a) 3–6% of 2,6-di-(ethylhexyl)naphthalate;
- (b) 3–6 of a C12–15 alkyl benzoate;
- (c) 15–18% of a 10% dimethicone copolyol in cyclomethicone; and
- (d) 0–1% of a volatile silicone (for example, a cyclomethicone such as a D5 cyclomethicone).

Internal Phase comprising
- (a) 12–15% of an antiperspirant active (on an anhydrous basis); and
- (b) a sufficient amount (35–55%) of a glycol component to dissolve the antiperspirant active and complete the internal phase;

wherein the ratio of the external phase to the internal phase is in the range of 1:1–1:4.

Formulation D

External Phase comprising
- (a) 8–12% of 2,6-di-(ethylhexyl)naphthalate;
- (b) 18–22% of a 10% dimethicone copolyol in cyclomethicone; and
- (c) 0–1% of a volatile silicone (for example, a cyclomethicone such as a D5 cyclomethicone).

Internal Phase comprising
- (a) 15–20% of an antiperspirant active (on an anhydrous basis); and
- (b) a sufficient amount of a glycol component (35–55%) to dissolve the antiperspirant active and complete the internal phase;

wherein the ratio of the external phase to the internal phase is in the range of 1:1–1:4.

Formulation E

External Phase comprising
- (a) 4–8% of an organic naphthalate ester (especially 2,6-di-(ethylhexyl)naphthalate);
- (b) 4–8% hydrogenated polyisobutene;
- (c) 4–8% of a 40% dimethicone copolyol in cyclomethicone; and
- (c) 6–10% of a volatile silicone (for example, a cyclomethicone such as a D5 cyclomethicone).

Internal Phase comprising
- (a) 15–20% of an antiperspirant active (on an anhydrous basis); and
- (b) a sufficient amount of a glycol component (for example, 35–55) to dissolve the antiperspirant active and complete the internal phase;

wherein the ratio of the external phase to the internal phase is in the range of 1:1–1:4.

Compositions of the present invention may be made by the techniques described in the Examples below. In general, the external and internal phases are formed separately using heating with the addition of a non-ionic emulsifier as needed. The alcohol component is added to the internal phase. The internal phase is added to the external phase very slowly. After the addition has been completed, the mixture is stirred at speeds on the order of 500–1000 rpm (for example, 1000 rpm), to achieve a homogeneous mixture, followed by homogenization at speeds which are correlated with a voltage setting of about 55–70, particularly 60, on a Powerstat Variable Autotransformer to achieve the target viscosity. Compositions with a viscosity of 0–50,000 centipoise, especially 5,000–20,000 centipoise, may be suitable for roll-on products while compositions having a viscosity on the order of 50–400,000 centipoise may be more suitable for soft solids or creams.

A variety of equipment and techniques may be used to obtain the compositions of the invention, including one pass homogenization, colloidal mill. Examples of such equipment include Sonic Production Sonolator 200-30, and Sonic Tri-Homo Colloid Mill both of which may be obtained from Sonic Corporation, Stratford, Conn.

It is believed that the more homogeneous the composition is and the more uniform the particle size, the better properties of the composition.

The cosmetic composition according to the present invention can be packaged in conventional containers, using conventional techniques. Where a gel, cream or soft-solid cosmetic composition is produced, the composition can be introduced into a dispensing package (for example, conventional packages for gels with glide on applicators, jars where the gel or cream is applied by hand, and newer style packages having a top surface with pores) as conventionally done in the art. Thereafter, the product can be dispensed from the dispensing package as conventionally done in the art, to deposit the active material, for example, on the skin. For roll-ons the compositions can be placed in a conventional type of container. This provides good deposition of the active material on the skin.

Throughout the present specification, where compositions are described as including or comprising specific components or materials, or where methods are described as including or comprising specific steps, it is contemplated by the inventors that the compositions of the present invention also consist essentially of, or consist of, the recited components or materials, and also consist essentially of, or consist of, the recited steps. Accordingly, throughout the present disclosure any described composition of the present invention can consist essentially of, or consist of, the recited components or materials, and any described method of the present invention can consist essentially of, or consist of, the recited steps.

Throughout the specification and claims all percents are in percents by weight based on the entire composition unless otherwise stated.

Compositions of the present invention can be formulated as clear, translucent or opaque products, although clear products are preferred. A desired feature of the present invention is that a clear, or transparent, cosmetic composition, (for example, a clear or transparent deodorant or antiperspirant composition) can be provided. The term clear or transparent according to the present invention is intended to connote its usual dictionary definition; thus, a clear, gel antiperspirant composition of the present invention allows ready viewing of objects behind it. By contrast, a translucent composition, although allowing light to pass through, causes the light to be scattered so that it will be impossible to see clearly objects behind the translucent composition. An opaque composition does not allow light to pass therethrough. Within the context of the present invention, a gel or liquid is deemed to be transparent or clear if the maximum transmittance of light of any wavelength in the range 400–800 nm through a sample 1 cm thick is at least 35%, preferably at least 50%. The gel or liquid is deemed translucent if the maximum transmittance of such light through the sample is between 2% and less than 35%. A gel or liquid is deemed opaque if the maximum transmittance of light is less than 2%. The transmittance can be measured by placing a sample of the aforementioned thickness into a light beam of a spectrophotometer whose working range includes the visible spectrum, such as a Bausch & Lomb Spectronic 88 Spectrophotometer. As to this definition of clear, see European Patent Application Publication No. 291,334 A2. Thus, according to the present invention, there are differences between transparent (clear), translucent and opaque compositions.

EXAMPLES

The following Examples are offered as illustrative of the invention and are not to be construed as limitations thereon. In the Examples and elsewhere in the description of the invention, chemical symbols and terminology have their usual and customary meanings. In the Examples as elsewhere in this application values for n, m, etc. in formulas, molecular weights and degree of ethoxylation or propoxylation are averages. Temperatures are in degrees C unless otherwise indicated. As is true for the rest of the application as well, the amounts of the components are in weight percents based on the standard described; if no other standard is described then the total weight of the composition is to be inferred. Where alcohol is listed, anhydrous alcohol with a denaturant was used unless otherwise indicated. Various names of chemical components include those listed in the *CTFA International Cosmetic Ingredient Dictionary* (Cosmetics, Toiletry and Fragrance Association, Inc., 7$^{th}$ ed. 1997). Viscosities are measured using Brookfield viscometers unless otherwise indicated. While specific amounts of particular elastomers have been described, there are chemical differences in the variety of elastomers that are available. The use of different elastomers may result in the need to increase or decrease the amount of elastomer used in a particular formulation, especially if a clear product is desired.

Example 1

General Method—No Elastomer

In general, the external and internal phases are formed separately either at room temperature or with heating as described below. The internal phase is added to the external phase very slowly while stirring at to form an emulsion. After the addition has been completed, the mixture is stirred at higher speed to achieve a homogeneous mixture. The final formula viscosity is then achieved by homogenizing the emulsion under either batch or continuous process conditions as described below. The fragrance may be added at any time during the process prior to final homogenization.

Preparation of External Phase

The ingredients to be used in the external phase are weighed out at room temperature and combined in a suitable vessel such as a 2 liter glass beaker. The mixture is stirred at about 500 rpm for 15–20 minutes using an overhead mixer such as a Lightnin Mixer Model L1003. If a waxy or solid emollient is to be added to the external (also called continuous) phase, the mixture may be heated to facilitate dissolution while stirring then cooled to room temperature prior to combination with internal phase as described below. The fragrance may be added to the external phase if desired.

Preparation of Internal Phase

The internal dispersed phase is prepared as described below. Ingredients are mixed for a time sufficient to achieve homogeneity. The antiperspirant active used (for example, Westchlor A2Z4105 (28% aluminum-zirconium glycinate in propylene glycol)) is weighed into a large beaker equipped with an overhead stirrer. Other internal phase ingredients are then added while stirring. The fragrance (if any is used) is added last and may be added either to the internal phase or the external phase or the final formula prior to homogenization. For many of the examples described here, one could add the fragrance to the internal phase.

If an optional non-ionic emulsifier such as Oleath-20 is used, the emulsifier and propylene glycol are combined in a separate beaker and heated to 40 degrees C. with stirring until the non-ionic emulsifier completely dissolved. The heat is turned off and the remaining ingredients to be used in the internal phase, including the antiperspirant active are weighed out and added to the mixture of propylene glycol and non-ionic emulsifier.

Preparation of the Emulsion

The internal phase made as described above is then added to the external phase over the course of 15–30 minutes while stirring at a speed of 500–1000 RPM. After the addition is complete, the mixture is stirred at 1000–1300 rpm for 20 minutes using a Lightnin Mixer Model L1003. The mixture is then homogenized for 2–4 minutes using a homogenizer from Greerco Corp., Hudson, N.H. at a reading of about 60 on a Powerstat Variable Autotransformer from Superior Electric Co., Bristol, Conn.

Further Processing

The product is then further processed by homogenized to achieve the desired final viscosity. This can be done by using a Gilford-Wood Model 1-L (Greerco Corp., Hudson, N.H.) homogenizer. The homogenizer speed is controlled by a Powerstat Variable Autotransformer Type 3PN116B (Superior Electronic. Co., Bristol, Conn.). Typical voltage setting and processing time are chosen to give a desired final formula viscosity.

An other method of homogenization of the final product is to pass the emulsion through a colloid mill such as a Sonic Tri-Homo Colloid Mill or a process sonolator such Sonic Production Sonolator 200-30 both available from Sonic Corporation of Stratford, Conn. Process conditions are chosen to give the desired final product viscosity. Unless otherwise specified, all conductivity is in micro Siemens and conductance is in micro Siemens/cm/ml.

Example 1A

An emulsion is made as follows. The ingredients to be used in the external phase are weighed out at room temperature and placed in a suitable vessel such as a 2 liter glass beaker. These ingredients include cyclomethicone and dimethicone copolyol (45–49% dimethicone copolyol in cyclomethicone, DOW CORNING®2-5185C diluted to a selected concentration); and 2,6-di-(ethylhexyl)naphthalate (Hallbrite TQ). The mixture is stirred at about 500 rpm for 15–20 minutes. For the internal phase the selected amount of non-ionic emulsifier (if used, such as Oleath-20) and propylene glycol is measured out and placed in a separate beaker of suitable size. The propylene glycol or mixture of non-ionic emulsifier (if used, such as Oleath-20) and propylene glycol is heated to 40 degrees C with stirring until the non-ionic emulsifier completely dissolved. The heat is turned off and the remaining ingredients to be used in the internal phase (including the antiperspirant active) is weighed out and added to the mixture of propylene glycol (or mixture of non-ionic emulsifier and propylene glycol). The internal phase is mixed well. The alcohol is added to the active phase. The fragrance (if any is used) is added last and may be added either to the internal phase, the external phase and/or the final emulsion. For the examples described here, one would frequently add the fragrance to the internal phase. The internal phase is then added to the external phase at a very slow rate. After the addition is complete, the mixture is stirred at 1000 rpm for 20 minutes using a Lightnin Mixer (Model L1003). The mixture is then homogenized for 10 minutes using a homogenizer from Greerco Corp., Hudson, N.H. at a reading of about 60 on a Powerstat Variable Autotransformer. The method is generally conducted at room temperature, except for the heating that is need when a solid or waxy emollient is added. If water, salt water or ethanol is added to the formulation, it is added to the active phase before the emulsification process. After the composition is made, the Brookfield and Carri-Med viscosities may be measured.

Example 2
General Method with Elastomer

The Method of Example 1 (or Example 1 as applied to Example 1A) can be repeated with the addition of an elastomer component. The elastomer component is obtained as a suspension of elastomer in cyclomethicone (for example at a concentration of 5.8% active in D5 cyclomethicone). The elastomer component is added to the silicone phase with stirring at high speed (800–1000 rpm for a 1 kilogram batch) until no particles of elastomer are visible to the eye.

Examples 121, 101, 106, 108, and 112

The method of Example 1 as refined by Example 1A can be used to make the following samples with the percentages of ingredients as listed. The batches are 0.5 kilograms.

TABLE A

| Ingredient | Ex. 121 | Ex. 101 | Ex. 106 | Ex. 108 | Ex. 112 |
|---|---|---|---|---|---|
| 10% copolyol (DC 5225C) | | | | 19.9 | 10 |
| 40% dimethicone copolyol (Dow Corning 2-5185 diluted to 40%) | 5 | 5 | 5 | | |
| C12–15 alkyl benzoate (Finsolv TN) | 16 | 0 | 0 | 0 | 0 |
| 2,6-di(ethylhexyl)-naphthalate (RX 13752) | 0 | 13.3 | 10.1 | 10.1 | 10.75 |
| Cyclomethicone (DC 245 (D5)) | 9 | 11.7 | 14.9 | 0 | 4.25 |
| Antiperspirant active (28%) (Westchlor 4105) | 58 | 68.5 | 58 | 58 | 68 |
| Alcohol SDA 40 (100%) | 10.5 | 0 | 10.5 | 10.5 | 5.5 |
| Oleth-20 | 0.5 | 0.5 | 0.5 | 0.5 | 0.5 |
| Fragrance | 1.0 | 1.0 | 1.0 | 1.0 | 1.0 |

Examples 18, 131, and 95

Examples 18, 131 and 95 are made using the method described in Example 1 and the amounts of ingredients described in Table B. The batch sizes are 0.5 kilograms. Note the use of an extra glycol component in these examples.

TABLE B

| Ingredient | Ex. 18 | Ex. 131 | Ex. 95 |
|---|---|---|---|
| 10% copolyol (DC 5225C) | | 16 | |
| 40% dimethicone copolyol (Dow Corning 2-5185 diluted to 40%) | 5 | 0 | 5 |
| C12–15 alkyl benzoate (Finsolv TN) | 15.5 | 4.5 | 0 |
| 2,6-di(ethylhexyl)-naphthalate | 0 | 4.5 | 0 |
| Cyclomethicone (DC 245 (D5)) | 9.5 | 0 | 1 |
| Antiperspirant active (28% in propylene glycol) (Westchlor 4105) | 53.57 | 53.57 | 53.57 |
| Propylene glycol | 5.33 | 0 | 6.08 |
| Methyl propylene glycol | 0 | 9.93 | 0 |
| Alcohol SDA 40 200 | 9.6 | 10.5 | 9.12 |
| Oleth-20 | 0.5 | 0 | 0 |
| Fragrance | 1.0 | 1.0 | 1.0 |
| Tween 80 | 0 | 0 | .23 |
| Elastomer[a] (5.8% actives in D5 cyclomethicone) | 0 | 0 | 8.5 |

[a]Elastomer as described in U.S. Pat. No. 6,060,546 at a concentration of 5% solids in cyclomethicone.
This patent is incorporated by reference for the description of the elastomer.

Example 3

Evaluation of Viscosity

Brookfield Viscosity

Viscosity can be measured using a Brookfield instrument (Model DV 11+) with an E Spindle at 2.5 revolutions per minute (rpm) and a setting of S 95. Units are in centipoise ("cps").

Carri-Med Viscosity

A second way of evaluating rheology is with the use of Carri-Med equipment to obtain complex viscosity. Rheological parameters can be measured using a Carri-Med CSL 100 instrument with parallel plates. Initially the zero gap is set on the instrument. A sample of approximately 5 grams is placed on the stage of the instrument. A 15 minute compression is used for sample equilibration. The excess of the sample is scraped around the plate geometry. The Theological parameters G, G", tan (delta) and complex viscosity (n*) can be measured by torque sweep experiments. An acrylic plate 6 cm in diameter can be used. A gap (1000 microns) is used between the two plates. Temperature is maintained at 23 degrees C. The oscillation stress can be varied from 2.358 Pa to 50.74 Pa with an oscillation frequency kept constant at 1 Hertz.

Data that should be obtained for the Examples described above is listed in Tables C and D.

TABLE C

Brookfield Viscosity

| Example Number | Initial Viscosity (centipoise) | Viscosity after 1 week at 49 degrees C | Viscosity after 4 weeks at 49 degrees C |
|---|---|---|---|
| 121 (control) | 160,000 | 30,000 | |
| 101 | 320,000 | | 310,000 |
| 106 | 230,000 | | 230,000 |
| 108 | 80,000 | | 85,000 |
| 112 | 85,000 | | 85,000 |
| 131 | 128,000 | 65,000 | |

TABLE D

Carri-Med Viscosity
Viscosity measurements are taken at angular frequency of 6.287 rad/sec;
temperature of 23 degrees C; and oscillation stress of 4.5 Pa. Data is
in Pa sec.

| Sample | Initial Complex Viscosity | Complex Viscosity after 1 week at 49° C. | Complex Viscosity after 4 weeks at 49° C. |
|---|---|---|---|
| 121 (control) | 99.5 | 3 | |
| 18 (control | 86 | 20 | 20 |
| 101 | 230 | 222 | 245 |
| 106 | 235 | | 205 |
| 108 | 75 | | 84 |
| 112 | 112 | | 80 |

Example 4
Measurement of Conductivity

As described above, measurement of conductivity and/or conductance is a way of evaluating the release of active from the composition and is deemed to be predictive of efficacy. Several methods have been described above each of which measures the increase in conductivity or conductance of a water drop placed on the surface of a sample film having a thickness of 100 microns. The increase in conductivity or conductance is due to the diffusion of the antiperspirant active salt from the test sample into the water drop. Each method is indicative of the relative bioavailability of the active salt at the time of first contact with sweat. For example, either method may be performed on samples which have been placed in the test wells and equilibrated for 2 hours in an environment of 37 degrees C. and 80% relative humidity (simulation of underarm conditions.

For the Examples described above, the expected conductivity at 10 seconds using the Standard Test are as follows.
Sample 101—2206 micro Siemens.
Sample 106—2469 micro Siemens.
Sample 121 (control)—1669 micro Siemens.
Sample 108—2843 micro Siemens.
Sample 112—1577 micro Siemens.
Sample 131—2577 micro Siemens.
Sample X=Lady Speed Stick Antiperspirant—1627 micro Siemens.
Sample 95 —a conductance at 10 seconds of 154 micro Siemens.

Note that the Sample 121 does not retain viscosity, indicating that it is not as stable as the naphthalate formulations. The data for Sample X shows that compositions of the invention can e expected to give efficacy comparable to stick products.

Example 4

The method of Example 1 as refined by 1A can be repeated with the types and amounts of ingredients listed in Table I. Viscosity measurements can be taken as described in Example 1 and the data also should be that as in Table E.

TABLE E

| Ingredient | Example 4 |
|---|---|
| 48% dimethicone copolyol (Dow Corning 2-5185 diluted to 40%) | 5 |
| 2,6-di-(ethylhexyl)naphthalate | 6 |
| Al—Zr gly in propylene glycol (28%) | 53.57 |
| Propylene glycol | 9.93 |
| cyclomethicone | 8 |

TABLE E-continued

| Ingredient | Example 4 |
|---|---|
| Hydrogenated polyisobutene | 6 |
| Alcohol (SDA 40) (100%) | 10.5 |
| Fragrance | 1% |
| Complex Viscosity (CarriMed) initial | 147 Pa sec |
| Complex Viscosity (CarriMed) after 4 weeks at 49 degrees C. | 112 Pa sec |

We claim:

1. An antiperspirant or deodorant composition comprising an emulsion wherein the emulsion comprises:
  (I) an external phase comprising:
    (a) 0.1–25% of an organic naphthalate ester having a refractive index in the range of 1.43–1.60 which is not soluble in alcohol or glycols in an amount greater than 1.0%,
    (b) a sufficient amount of a silicone copolyol to achieve a solids content of 0.25–10%, wherein the silicone copolyol may be added with or without solvent;
    (c) a sufficient amount of a volatile silicone to achieve a total amount of the external phase as 15–33; and
    (d) 0–5% of a silicone elastomer; and
  (II) an internal phase comprising:
    (a) 0.1–30% of an antiperspirant active (on an anhydrous basis); and
    (b) a sufficient amount of a glycol component to dissolve the antiperspirant active and to complete the internal phase up to a maximum of 80% glycol component;
wherein the ratio of the external phase to the internal phase is in the range of 1:1–1:4 and all amounts are in percent by weight based on the total weight of the composition.

2. A composition according to claim 1 wherein the solids content of the silicone copolyol is in the range of 1.0–3.0%.

3. A composition according to claim 1 wherein the silicone copolyol is dimethicone copolyol with a cyclomethicone solvent.

4. A composition according to claim 1 wherein the external phase comprises 0.5–25% of the organic naphthalate ester.

5. A composition according to claim 1 wherein the external phase comprises 2.5–15% of the organic naphthalate ester.

6. A composition according to claim 1 wherein the organic naphthalate ester is 2,6-di-(ethylhexyl)naphthalate.

7. A composition according to claim 1 wherein the internal phase comprises up to 7% antiperspirant active and 50–80% glycol component.

8. A composition according to claim 1 wherein the internal phase comprises 7–25% of an antiperspirant active and 35–55% of a glycol component.

9. A compositions according to claim 1 which additionally comprises one or more members selected from the group consisting of 0–10% ethanol, 0–5% fragrance, and 0–5% of a non-ionic emulsifier.

10. A compositions according to claim 1 wherein the organic naphthalate ester is a monoester, diester or polyester of a naphthalene dicarboxylic acid, which is a reaction product of:
  (i) a naphthalene dicarboxylic acid having the structure: $HO_2C-Q-CO_2H$ where Q is a naphthalene; and
  (ii) an alcohol having the structure $R^1-OH$, or a diol having the structure $HO-R^2-OH$, or a polyglycol having the structure $HO-R-(-O-R^2-)_m-OH$, wherein $R^1$ is an alkyl group, straight chain or branched, having 1 to 22 carbon atoms, $R^2$ and $R^3$, may be the same or different, and are each an alkylene group, having 1 to 6 carbon atoms, and wherein m and n are each 1 to about 100, or a mixture thereof.

11. A composition according to claim 10 wherein the naphthalate ester is a diester having a structure of: $R^1O_2C-Q-CO_2R^1$.

12. A composition according to claim 10 wherein the naphthalate ester has a structure of Formula I:

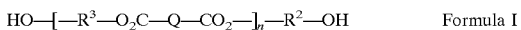    Formula I wherein $R^2$ and $R^3$, may be the same or different, are each an alkylene group having 1 to 6 carbon atoms, and n=1 to about 100.

13. A composition according to claim 10 wherein the naphthalate ester is a diester having a structure of Formula II:

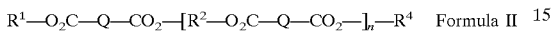    Formula II wherein $R^1$ and $R^2$ and n are as defined in Formula I, and $R^4$ is independently selected from the same group as defined for $R^1$ in Formula I.

14. A composition according to claim 10 wherein the naphthalene dicarboxylic acid is selected from the group consisting of:

1,2-naphthalene dicarboxylic acid; 1,3-naphthalene dicarboxylic acid; 1,4-naphthalene dicarboxylic acid; 1,5-naphthalene dicarboxylic acid; 1,6-naphthalene dicarboxylic acid; 1,7-naphthalene dicarboxylic acid; 1,8-naphthalene dicarboxylic acid; 2,3-naphthalene dicarboxylic acid; 2,6-naphthalene dicarboxylic acid; 2,7-naphthalene dicarboxylic acid, and mixtures thereof.

15. A composition according to claim 10 wherein the alcohol $R^1$—OH is selected from the group consisting of methanol, ethanol, propanol, isopropyl alcohol, n-butanol, sec-butanol, isobutyl alcohol, tert-butyl alcohol, amyl alcohol, 1-hexanol, 1-octanol, 1-decanol, isodecyl alcohol, 1-undecanol, 1-dodecanol, 1-tridecyl alcohol, 1-tetradecanol, 1-hexadecanol, 1-octadecanol, 1-eicosonol, 1-decosonol, 2-ethylhexyl alcohol, 2-butyloctanol, 2-butyldecanol, 2-hexyldecanol, 2-octyldecanol, 2-hexyldodecanol, 2-octyldodecanol, 2-decyltetradecanol, and mixtures thereof.

16. A composition according to claim 10 wherein the glycol or polyglycol is selected from the group consisting of ethylene glycol, propylene glycol, 1,2-propanediol, diethylene glycol, triethylene glycol, tetraethylene glycol, dipropylene glycol, tripropylene glycol, methyl propanediol, 1,6-hexanediol, 1,3-butanediol, 1,4-butanediol, PEG-4 through PEG-100, PPG-9 through PPG-34, pentylene glycol, neopentyl glycol, trimethylpropanediol, 1,4-cyclohexanedimethanol, 2,2-dimethyl-1,3-propanediol, 2,2,4,4-tetramethyl-1,3-cyclobutanediol, and mixtures thereof.

17. A composition according to claim 1 which contains cyclomethicone.

18. A composition according to claim 1 further comprising an elastomer.

19. A composition according to claim 18 wherein the elastomer is selected from the group consisting of cetearyl dimethicone/vinyl dimethicone crosspolymers; cyclomethicone (and) dimethicone/vinyl dimethicone crosspolymers; dimethicone/vinyl dimethicone crosspolymers; a mixture of cyclomethicone and stearyl-vinyl/hydromethylsiloxane copolymers; and vinyl dimethicone crosspolymers selected from the group consisting of (a) cyclomethicone (and) dimethicone/vinyl dimethicone crosspolymer; (b) dimethicone (and) dimethicone/vinyl dimethicone crosspolymer; (c) cyclomethicone (and) dimethicone/vinyl dimethicone crosspolymer; (d) (phenyl trimethicone (and) dimethicone/phenyl vinyl dimethicone crosspolymer; and (e) dimethicone copolyol crosspolymer.

20. A composition according to claim 1 comprising:
an external phase comprising:
(a) 3.0–15% of 2,6-di-(ethylhexyl)naphthalate;
(b) 1.5–3.0% of a 48% dimethicone copolyol in cyclomethicone or its equivalent;
(c) 4.0–16% of a volatile silicone; and
(d) 0–1 % of a silicone elastomer.
an internal phase comprising:
(a) 9.0–20% of an antiperspirant active (on an anhydrous basis); and
(b) 35–55% of a glycol component to dissolve the antiperspirant active;
wherein the ratio of the external phase to the internal phase is in the range of 1:1–1:4.

21. A composition according to claim 1 comprising:
an external phase comprising:
(a) 10–15% of 2,6-di-(ethylhexyl)naphthalate;
(b) 2–3% of a 40% dimethicone copolyol in cyclomethicone; and
(c) 8–10% of a volatile silicone;
an internal phase comprising:
(a) 12–15% of an antiperspirant active (on an anhydrous basis); and
(b) 30–39% of a glycol component to dissolve the antiperspirant active;
wherein the ratio of the external phase to the internal phase is in the range of 1:1–1:4.

22. A composition according to claim 1 comprising:
an external phase comprising:
(a) 3–6% of 2,6-di-(ethylhexyl)naphthalate;
(b) 15–18% of a 10% dimethicone copolyol in cyclomethicone; and
(c) 0–1% of a volatile silicone;
(d) 3–6% of a C12–15 alkyl benzoate;
an internal phase comprising:
(a) 12–15% of an antiperspirant active (on an anhydrous basis); and
(b) 35–55% of a glycol component to dissolve the antiperspirant active;
wherein the ratio of the external phase to the internal phase is in the range of 1:1–1:4.

23. A composition according to claim 1 comprising:
an external phase comprising:
(a) 8–12% of 2,6-di-(ethylhexyl)naphthalate;
(b) 18–22% of a 10% dimethicone copolyol in cyclomethicone; and
(c) 0–1% of a volatile silicone;
an internal phase comprising:
(a) 15–20% of an antiperspirant active (on an anhydrous basis); and
(b) 35–55% of a glycol component to dissolve the antiperspirant active;
wherein the ratio of the external phase to the internal phase is in the range of 1:1–1:4.

24. A composition according to claim 1 comprising:
an external phase comprising:
(a) 4–8% hydrogenated polyisobutene;
(b) 4–8% of a 40% dimethicone copolyol in cyclomethicone; and
(c) 6–10% of a cyclomethicone;
an internal phase comprising:
(a) 15–20% of an antiperspirant active (on an anhydrous basis); and
(b) 35–55% of a glycol component to dissolve the antiperspirant active;
wherein the ratio of the external phase to the internal phase is in the range of 1:1–1:4.

* * * * *